US009465135B2

(12) United States Patent
Morton

(10) Patent No.: US 9,465,135 B2
(45) **Date of Patent: *Oct. 11, 2016**

(54) HIGH ENERGY X-RAY INSPECTION SYSTEM USING A FAN-SHAPED BEAM AND COLLIMATED BACKSCATTER DETECTORS

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/454,295

(22) Filed: Aug. 7, 2014

(65) Prior Publication Data

US 2015/0078519 A1 Mar. 19, 2015

Related U.S. Application Data

(63) Continuation of application No. 12/993,831, filed as application No. PCT/GB2009/001275 on May 20, 2009, now Pat. No. 8,831,176.

(30) Foreign Application Priority Data

May 20, 2008 (GB) .................................. 0809107.6

(51) Int. Cl.

| | |
|---|---|
| ***G01V 5/00*** | (2006.01) |
| ***G01N 23/203*** | (2006.01) |
| ***G01N 23/20*** | (2006.01) |

(52) U.S. Cl.
CPC ........... *G01V 5/0025* (2013.01); *G01N 23/203* (2013.01); *G01N 23/20083* (2013.01); *G01V 5/0016* (2013.01); *G01N 2223/053* (2013.01)

(58) Field of Classification Search
CPC ............ G01V 5/0025; G01V 5/0016; G01N 23/20083; G01N 23/203; G01N 2223/053
See application file for complete search history.

(56) References Cited

U.S. PATENT DOCUMENTS

| | | | | |
|---|---|---|---|---|
| 6,546,072 | B1 * | 4/2003 | Chalmers | 378/57 |
| 6,735,279 | B1 * | 5/2004 | Jacobs et al. | 378/86 |
| 8,831,176 | B2 * | 9/2014 | Morton | 378/86 |
| 2004/0017888 | A1 * | 1/2004 | Seppi et al. | 378/57 |
| 2007/0007455 | A1 * | 1/2007 | Juni | G01N 23/203 |
| 2007/0189454 | A1 * | 8/2007 | Georgeson et al. | 378/57 |

* cited by examiner

*Primary Examiner* — Glen Kao
*Assistant Examiner* — Chih-Cheng Kao
(74) *Attorney, Agent, or Firm* — Novel IP

(57) ABSTRACT

This invention provides a scanning system for scanning an object in a scanning zone. The scanning system includes both a radiation source arranged to irradiate the object with radiation having a peak energy of at least 900 keV and a scatter detector arranged to detect radiation scattered from the object wherein the radiation source is arranged to irradiate the object over a plurality of regions to be scanned within a single irradiation event. The scatter detector includes a plurality of detection elements, each detection element being arranged to detect scattered radiation from a predefined part of the scanning zone and a signal processor arranged to calculate scatter intensity across the plurality of detector elements.

14 Claims, 4 Drawing Sheets

28'
A
D1
D2
D3
D4
B
A
B

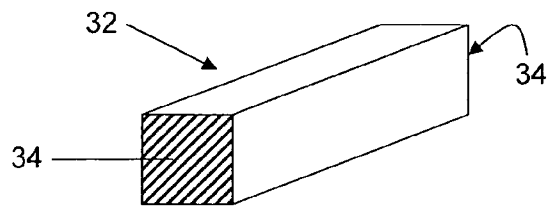
Figure 5
Figure 6
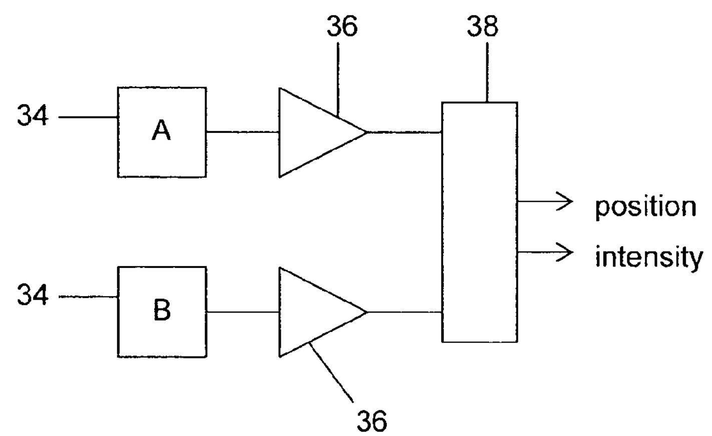
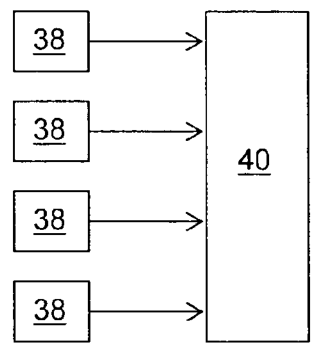
Figure 7

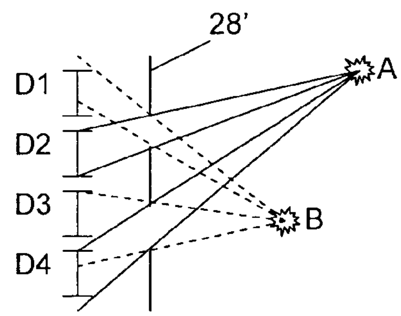
Figure 8
Figure 9
A
B
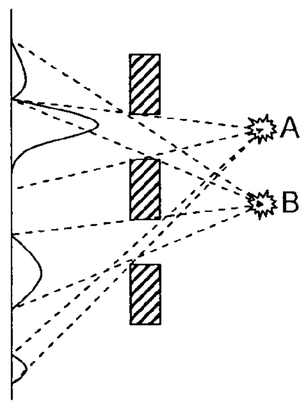
Figure 10
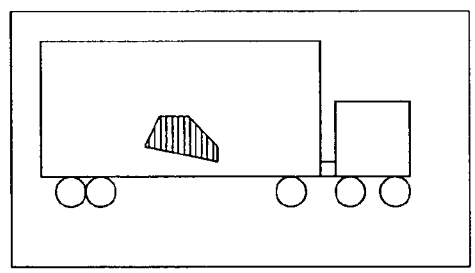
Figure 11

HIGH ENERGY X-RAY INSPECTION SYSTEM USING A FAN-SHAPED BEAM AND COLLIMATED BACKSCATTER DETECTORS

CROSS-REFERENCE TO RELATED APPLICATIONS

The present application is a continuation of U.S. patent application Ser. No. 12/993,831, entitled “High-Energy X-Ray Inspection System Using a Fan-Shaped Beam and Collimated Backscatter Detectors”, filed on Feb. 22, 2011, which is a national stage application of PCT/GB2009/001275, filed on May 20, 2009, which, in turn, relies on Great Britain Patent Application Number 0809107.6, filed on May 20, 2009. All priority applications are herein incorporated by reference in their entirety.

FIELD OF THE INVENTION

The present application relates to scanning systems. It has particular application in scanning systems for cargo, but can also be used in scanners for other applications such as security and high energy medical scanners. There exists a requirement for screening of cargo items for the detection of illicit materials and devices.

BACKGROUND

Increasingly frequently, scanning systems involve the use of high energy inspection equipment based on transmission imaging with X-radiation generated by an X-ray linear accelerator with typical beam quality of 1 MeV to 9 MeV.

Such systems are very effective at probing the structure and shape of relatively high atomic number articles but are less effective at locating the presence of low atomic number materials in sheet like configurations that are broadly perpendicular to the path of the incoming X-ray beam.

FIG. 1 is a schematic representation of a known system 2. The known system 2 comprises an x-ray source, in the form of a rotating disc x-ray source 4. An object to be scanned is shown in the form of a lorry 8. A detector 6 is arranged on the same side of the lorry as the source. The source is arranged to irradiate a single region of the object at any one time (i.e. in any one irradiation event or burst). The source produces a tightly collimated beam 10 which irradiates a point on the object 8. Scattered radiation 12 is scattered in all directions and is detected at the detector 6. The detector 6 measures the amount of radiation per irradiation event in order to provide information on the point of the object being irradiated during that event.

The inverse square law indicates that the intensity of a radiation beam reduces in proportion to the square of the distance from the source. For example, the source intensity (photons/unit area) drops by a factor of four in moving from 10 cm away from a point source of radiation to the same area 20 cm away. Therefore, the strength of the backscatter signal drops rapidly with distance into the cargo and so X-ray backscatter is predominantly a surface inspection technique.

Further, it can easily be shown that the maximum energy of a backscattered X-ray photon is 256 keV. This relatively low energy X-ray is absorbed rather readily by high density materials such as steel, again suggesting that X-ray backscatter imaging is predominantly a surface imaging method.

Therefore, what is needed is an X-ray backscatter imaging that is integrated with high intensity linear accelerator based transmission imaging in order to spatially correlate surface X-ray backscatter imaging with bulk object transmission imaging as a further investigation in detection of illicit materials and objects in cargo items.

SUMMARY OF THE INVENTION

In some embodiments of the present invention, it is recognised that there is advantage in combining X-ray backscatter imaging with high intensity linear accelerator based transmission imaging in order to spatially correlate surface X-ray backscatter imaging with bulk object transmission imaging as a further investigation in detection of illicit materials and objects in cargo items.

In one embodiment, the present invention provides a scanning system for scanning an object in a scanning zone. The system comprises a radiation source arranged to irradiate the object with radiation having a peak energy of at least 900 keV. The system also comprises a scatter detector arranged to detect radiation scattered from the object wherein the radiation source is arranged to irradiate the object over a plurality of regions to be scanned within a single irradiation event. The scatter detector comprises a plurality of detection elements, each detection element being arranged to detect scattered radiation from a predefined part of the scanning zone and a signal processor arranged to calculate scatter intensity across the plurality of detector elements.

BRIEF DESCRIPTION OF THE DRAWINGS

Embodiments of the invention will now be described, by way of example only, with reference to the accompanying drawings in which:

FIG. 5 schematically shows a detector element according to an embodiment of this invention;

FIG. 6 illustrates a circuit for converting the detector element output position-sensitive according to an embodiment of this invention;

FIG. 7 illustrates a circuit for calculating scatter intensity across the detector elements;

FIGS. 8 to 10 graphically illustrate the effect of different types of zone plate on backscatter radiation distribution; and FIG. 11 is a representation of a display output according to the invention and visible by an operator of the scanning system.

DETAILED DESCRIPTION OF THE DRAWINGS

The present invention is directed towards combining X-ray backscatter imaging with high intensity linear accelerator based transmission imaging in order to spatially correlate surface X-ray backscatter imaging with bulk object transmission imaging as a further investigation in detection of illicit materials and objects in cargo items.

In this situation, X-ray backscatter imaging can be a useful addition to the diagnostic arsenal. Known systems tend to utilise a tightly collimated radiation beam that is scanned mechanically across the region of interest with a large area detector positioned to capture as many as possible of the backscattered X-ray photons. An image can be formed by correlating the count rate from the detector with the known point of intersection of the X-ray beam with the item under inspection.

The independent claims define aspects of the invention for which protection is sought. The dependent claims define preferable inventive features. Any of the features of the dependent claims may be used in combination with the features of other claims, even if they are not explicitly dependent upon them—this will be clear to a person skilled in this field. Where a feature is claimed in one category (e.g. method, system, detector arrangement, etc.) protection is sought for that feature in other categories even if not explicitly claimed.

Figure 1:
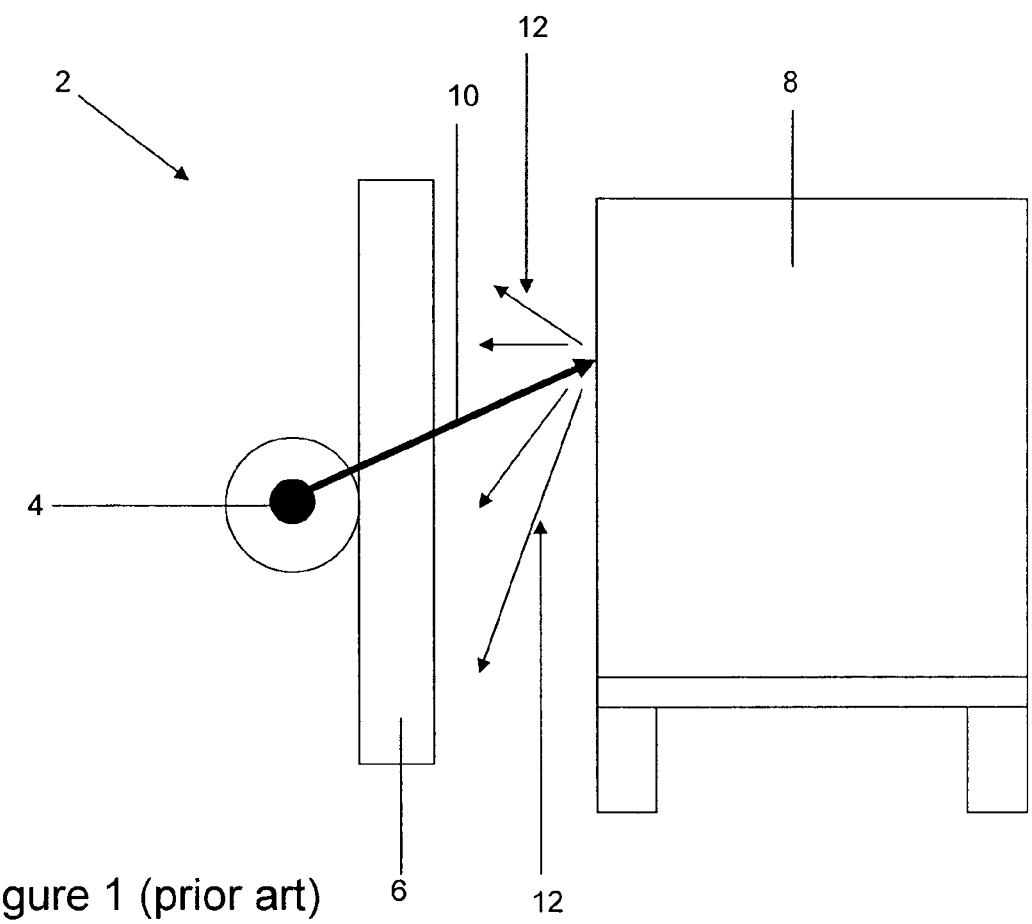
FIG. 1 schematically shows a prior art scanning system.
Figure 2:
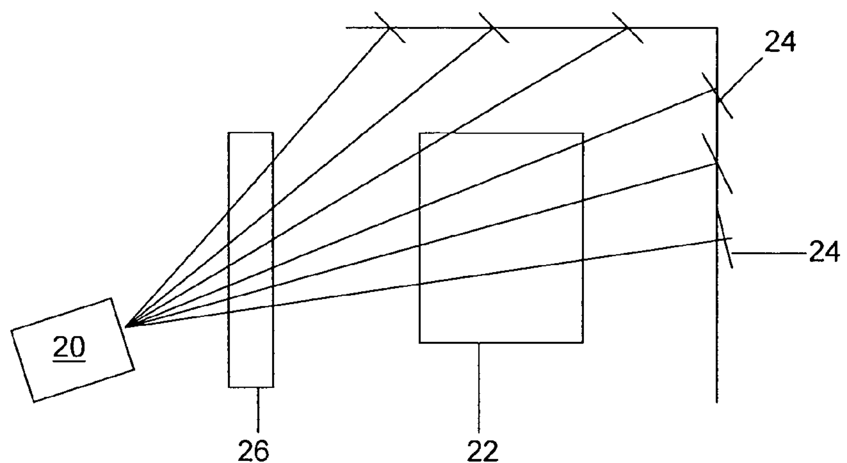
FIGS. 2 to 4 schematically show parts of a scanning system according to an embodiment of this invention.
Figure 3:
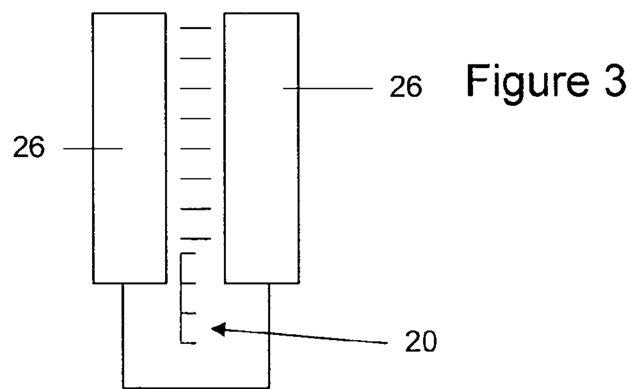
Figure 4:
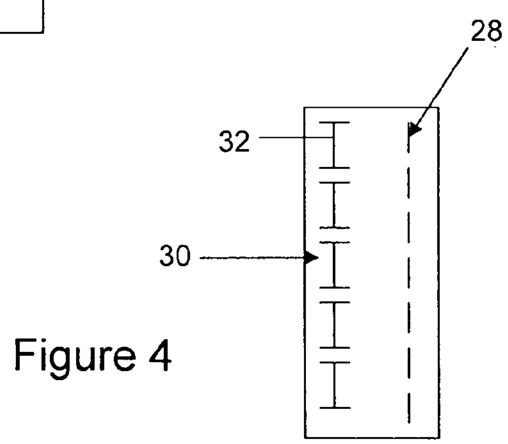

A system configuration according to an embodiment of the invention is outlined in FIGS. 2 to 4. Here, an X-ray linear accelerator 20 is used to fire a collimated fan-beam of high energy (at least 900 keV) X-radiation through an object 22 under inspection and so to a set of X-ray detectors 24 which can be used to form a high resolution transmission X-ray imaging of the item under inspection. The X-ray linear accelerator beam is pulsed, so that as the object under inspection moves through the beam, the set of one-dimensional projections can be acquired and subsequently stacked together to form a two-dimensional image.

In this embodiment, an X-ray backscatter detector 26 is placed close to the edge of the inspection region on the same side as the X-ray linear accelerator 20 but offset to one side of the X-ray beam so that it does not attenuate the transmission X-ray beam itself. As shown in FIG. 3, it is advantageous to use two backscatter imaging detectors 26, one on either side of the primary beam. In some embodiments the backscatter detectors may be arranged differently. In some embodiments there may be only one backscatter detector. In other embodiments there may be more than two such detectors.

In contrast to known backscatter imaging detectors which use the localisation of the incident X-ray beam to define the scattering region, the backscatter imaging detector described here is able to spatially correlate the intensity of backscattered X-ray signals with their point of origin regardless of the extended fan-beam shape of the X-ray beam.

In the backscatter imaging detector 26 of this embodiment, this spatial mapping is performed using a segmented collimator 28 in zone plate configuration as shown schematically in FIG. 4. Normally, a zone plate will comprise a series of sharply defined patterns whose impulse response function is well known in the plane of a two-dimensional imaging sensor that is located behind the sensor. In the present case, the energy of the X-ray beam to be detected is typically in the range 10 keV to 250 keV and so the edges of the zone plate pattern will not be sharp. For example, a zone plate fabricated using lead will require material of thickness typically 2 mm to 5 mm. Further, it is expensive to fabricate a high resolution two-dimensional imaging sensor of the size that is required in this application.

However, it is noted that the radiation beam is well collimated in one direction (the width of the radiation fan beam) and therefore the imaging problem is reduced to a one-dimensional rather than a two-dimensional problem. Therefore a backscatter detector in the form of an effectively one dimensional imaging sensor 30 is provided behind the zone plate 28. To address this problem an elemental backscatter detector is used in this embodiment. As shown in FIG. 4, the detector 30 comprises a plurality of detector elements 32. FIG. 5 illustrates a detector element 32 suitable for use in this example. Here, the detector element 32 comprises a bar of scintillation material (about 100 mm long in this example) and is supplied with a photo-detector 34 at either end. The photo-detector 34 may advantageously be a semiconductor photodiode or a photomultiplier tube. X-ray photons that interact in the scintillation material emit light photons and these will travel to the two photo-detectors where they may be detected. It may be shown that the intensity of the light reaching each photo-detector is in proportion to the distance of the point of interaction from the face of the photo-detector. Therefore, by measuring the relative intensity at the two photo detectors, the point of interaction of the X-ray photon with the detector can be resolved.

A suitable circuit for resolving the position of interaction is shown in FIG. 6. Here each photo detector 34 is connected to its own amplifier 36 whose analogue output is fed into a position logic block 38. In this block, the magnitude of the output from each detector is digitised and the resulting digital values are ratioed in order to find the point of interaction. The sum of the two outputs gives the total energy deposited in the detector during the interaction.

The basic principle of operation of a zone plate 28' is described in FIG. 8. Consider a radiation source at point A. Radiation from this source will pass through apertures in the zone plate resulting in exposure of the detectors. The masking effect of the zone plate 28' is to cause exposure of detectors D2 and D4 in this example with no exposure of detectors D1 and D3. However, radiation from source point B results in exposure to detectors D1 and D3 with no exposure of detector D2 and little exposure on detector D4. An algorithm can therefore be determined that analyses the pattern of detector exposures to allocate each measured pattern with a particular radiation source position.

In the chosen embodiment, things are a bit more complex since the X-ray linear accelerator is a pulsed source with a pulse width of typically 5 μs and a dead time between pulses of typically 10 ms. Therefore, scatter data for all points in the object under inspection will be received simultaneously and standard analysis of the detector data will not yield a reasonable result.

In the present invention, it is recognised that, due to the inverse square law, the intensity of the backscattered signal at the detector is to first order matched by the distribution of scattering objects immediately opposite to the detector. This is illustrated in FIG. 9. Therefore, a position resolving detector can to first order determine the scatter profile from the object under inspection even in the absence of any collimation. The closer the scattering object is to the detector, the sharper the spatial resolution of the data and the higher the count rate at the detector.

If a coarse collimator is then added as shown in FIG. 10, further information can be determined to sharpen up the scatter signal, but at the expense of overall detected signal. In this stylised diagram, the signal from source point A is now better defined, but the signal from source point B is all but attenuated away by the collimator. In practice, there is a trade-off between detection efficiency and image resolution and this is affected by practical issues such as acceptable dose levels, cost and complexity.

In this embodiment however, a data acquisition system is required of the form shown in FIG. 7 where data from each detector element (generally in the form of position and intensity) is interpreted by a signal processor 40 in order to calculate a one-dimensional scatter intensity distribution along the length of the fan-beam of X-rays that passes through the object under inspection.

In a further aspect of this invention, transmission X-ray data that is collected simultaneously with the scatter information can be used to constrain the activity of the signal processor shown in FIG. 7 by providing a-priori information as to the location and extent of objects that may constitute a scattering object. This high quality spatial information can be used to prepare the scatter image data for operator review on a workstation screen, for example.

A base level of X-ray scattering will be observed across the whole image and this information is both anticipated and uninteresting. What is of relevance to the operator is to resolve significant changes in the X-ray backscatter signal that may denote the presence of an illicit material or device. Therefore, in a further aspect of this invention, the signal processor can be used to subtract a base-line offset from all X-ray backscatter signals such that the remaining data contains only significant scatter signal. The signal processor should include the ability to filter the X-ray backscatter signals to ensure that only significant information is passed onto the operator workstation screen as shown overlaid on the transmission X-ray image in FIG. 11.

A suitable statistically driven noise filtering algorithm will take the mean and variance in the backscatter signal from all detector elements and compare these against background levels. When a statistically significant difference is seen between the signal at a given detector and that in the background, the signal is passed through to the output otherwise the signal is set to zero. A statistically significant difference is one where the detected signal is greater than a constant multiple of the background standard deviation. A suitable constant would be one standard deviation above background.

In another embodiment of this invention, the signal processor will provide two-dimensional statistical filtering of the X-ray backscatter signal with a dilate-erode based image segmentation algorithm to clearly localise and define the X-ray backscatter region.

The displayed X-ray backscatter image will advantageously be colour coded in order to provide an indication of the intensity of backscatter data which is loosely related to the density of the scattering object. The data must first be normalised to reflect the varying distance between the X-ray source and the edge of the scattering cargo item under inspection.

In some embodiments the object is irradiated with higher energy radiation, e.g. 1 MeV, 2 MeV, 3 MeV or higher etc.

In some embodiments different types of zone plates may be used—the skilled person will be able to ascertain form the teaching of this document suitable zone plate configuration.

Different detector elements may be used—for example different position sensitive detector elements.

I claim:

1. A scanning method for scanning an object in a scanning zone, the method comprising:

irradiating the object with an X-ray radiation source having a peak energy of at least 900 keV, wherein the object is irradiated over a plurality of regions to be scanned within a single irradiation event;

detecting X-ray radiation scattered from the object wherein said scattered X-ray radiation is detected from a predefined part of the scanning zone via a detector having a plurality of detector elements and wherein each detector element comprises a first photodetector, a second photodetector, and scintillator material positioned therebetween;

determining a point of interaction between photons of said X-ray radiation and said plurality of detector elements by obtaining a first output from the first photodetector and a second output from the second photodetector, and determining a ratio of said first and second outputs;

determining a pattern of detector exposures, wherein said pattern of detector exposures is created using a mask to create exposure patterns across multiple detection elements, said mask restricting scattered X-ray radiation that is not from a corresponding part of the scanning zone from reaching its corresponding detector region; and analyzing the pattern of detector exposures to allocate each exposure pattern with a particular radiation source position.

2. The method of claim 1 wherein the plurality of regions are adjacent to each other.

3. The method of claim 2 wherein the plurality of regions are linearly arranged.

4. The method of claim 1 wherein the object is moved relative to the X-ray radiation source such that a different plurality of regions is scanned with a different irradiation event.

5. The method of claim 4 wherein the different plurality of regions cover substantially the whole object or substantially all of the areas of interest on the object.

6. The method of claim 1 wherein the X-ray radiation source irradiates the object in discrete bursts and a single irradiation event comprises one of the discrete bursts.

7. The method of claim 1 wherein the scatter detector detects X-ray radiation from a plurality of regions to be scanned substantially simultaneously.

8. The method of claim 1 wherein the scatter detector detects X-ray radiation from the plurality of regions in response to the X-ray radiation source which is arranged to irradiate the object in discrete bursts.

9. The method of claim 1 wherein a distance between a detector region and its corresponding part of the scanning zone is minimized.

10. The method of claim 1 wherein the mask restricts scattered X-ray radiation from passing through it using a plate having apertures therethrough, wherein the apertures allow scattered X-ray radiation to pass through the mask.

11. The method of claim 10 wherein the apertures are arranged to correspond in position to the parts of the scanning zone such that each aperture is as close as possible to its corresponding part of the scanning zone.

12. The method of claim 1 wherein a transmission detector detects X-ray radiation which passes through the object and a controller receives and processes information from the transmission detector in order to identify regions of the object of particular interest.

13. The method of claim 12 wherein the controller superimposes the information received from the transmission detector upon information received from the scatter detector.

14. The method of claim 1 wherein an image of the object and of any regions of particular interest is generated and wherein superimposed information is used to create the image.

* * * * *